United States Patent [19]

Vanhauten

[11] 3,987,104
[45] Oct. 19, 1976

[54] PROCESS FOR PREPARING SATURATED KETONES AND A CATALYST FOR REALIZING THE PROCESS

[75] Inventor: Theodorus G. M. Vanhauten, Heerlen, Netherlands

[73] Assignee: Stamicarbon B.V., Geleen, Netherlands

[22] Filed: June 12, 1973

[21] Appl. No.: 369,389

[30] Foreign Application Priority Data
June 12, 1972 Netherlands .................... 7207938

[52] U.S. Cl. ........................... 260/597 R; 252/454
[51] Int. Cl.$^2$ ........................................ C07C 45/04
[58] Field of Search .................... 260/597 R

[56] References Cited
UNITED STATES PATENTS

| | | | |
|---|---|---|---|
| 2,874,191 | 2/1959 | Foreman et al. | 260/597 R |
| 3,171,859 | 3/1965 | Sennewald et al. | 260/597 R |
| 3,387,038 | 6/1968 | Koch | 260/604 R |
| 3,636,156 | 1/1972 | Ozaki et al. | 260/597 R |
| 3,789,063 | 1/1974 | Lane | 260/604 R |

FOREIGN PATENTS OR APPLICATIONS 2,329,212  1/1974  Germany ........................... 260/597

*Primary Examiner*—James O. Thomas, Jr.
*Assistant Examiner*—James H. Reamer
*Attorney, Agent, or Firm*—Cushman, Darby & Cushman

[57] ABSTRACT

An improved process for preparing ketones by contacting a mixture of an olefin and steam with a supported catalyst of tin oxide and molybdenum oxide on an inert, thermostable carrier is disclosed, wherein the supported catalyst contains at least one alkali metal or alkaline earth metal compound in an amount, calculated as metal, of 0.01 to 5% by weight, based on the weight of the carrier material. The formation of troublesome by-products is reduced by the use of the alkali metal and/or alkaline earth metal compound, with a resulting improvement in olefin conversion selectivity.

11 Claims, No Drawings

PROCESS FOR PREPARING SATURATED KETONES AND A CATALYST FOR REALIZING THE PROCESS

BACKGROUND OF THE INVENTION

The present invention relates to a process for preparing ketones by contacting an olefin with steam in the presence of a catalyst of tin oxide and molybdenum oxide on a thermostable carrier. The present invention also relates to the catalyst used in the process.

Commonly assigned U.S. patent application Ser. No. 88,467 discloses a process for producing, e.g., acetone and methylethyl ketone by contacting a mixture of propylene or butylene, respectively, with a supported catalyst of tin oxide and molybdenum oxide. Good reaction selectivity is obtained in the process of this copending application if the mixture of olefin and steam is contacted with the catalyst and thereafter the catalyst is treated for a short time with an oxygen-rich gas mixture. An oxygen-rich gas mixture is a gas mixture having at least sufficient oxygen content so that when the mixture contacts the catalyst, the oxygen content of the catalyst becomes higher. However, the reaction mixture produced by this copending application always contains, in addition to the desired saturated ketone corresponding to the initial olefin, various by-products, such as carbon monoxide, carbon dioxide, lower acids, unsaturated hydrocarbons formed through disproportionment, and oxidation products thereof, as well as oligomers of the initial olefin. The oligomers are considered particularly undesired by-products, since they partly deposit upon the catalyst, causing the catalyst activity to decrease over the course of the reaction, thereby resulting in decreased conversion. Furthermore, by-products having a boiling point approaching that of the desired ketone product are also troublesome, since these by-products interfer with the recovery of the desired ketone from the reaction mixture.

DESCRIPTION OF THE INVENTION

The present invention reduces the formation of troublesome by-products encountered by the copending application described hereinabove. A reduction of by-product formation considerably improves the selectivity of the olefin conversion. These desired results are obtained by incorporating small amounts of an alkali metal or an alkaline earth metal in the catalyst, which is based upon tin oxide and molybdenum oxide.

The process of the present invention involves contacting a mixture of olefin and steam with a supported catalyst of tin oxide and molybdenum oxide on a thermostable carrier material. The catalyst contains at least one metal compound which is an alkali metal or an alkaline earth metal, generally present in an amount, calculated as metal, of from 0.01 to about 5% by weight, based on the weight of the thermostable carrier material.

A catalyst of tin oxide and molybdenum oxide upon a inert thermostable carrier can be prepared by the process disclosed in the aforesaid copending application, Ser. No. 88,467, the disclosure of which is hereby incorporated by reference. An alkali metal and/or alkaline earth metal compound is then added to this catalyst, preferably in the form of a solution of a neutral salt having an anion which decomposes or volatilizes at a relatively low temperature, preferably less than 600° C. The nitrate anion is highly suitable. While the present invention is not to be limited to any particular theory, it is believed that the alkali metal and/or alkaline earth metal is converted into the form of the corresponding oxide. Other suitable anions include the formates, the acetates and the oxalates and other organic acid compounds.

All of the alkali metals and alkaline earth metals exert a favorable influence upon the olefin conversion in the process of the present invention. Among preferred metals may be mentioned sodium, potassium and calcium. Mixtures of alkali and/or alkaline earth metals may be used if desired. Generally, the alkali metal or alkaline earth metal will be used in an amount, calculated as metal, of about 0.01 to about 5% by weight, based on the weight of the carrier material. It is particularly preferred to use an amount of alkali metal and/or alkaline earth metal of about 0.5 to 2% by weight, based on the weight of the carrier material.

The olefins which are converted into the corresponding saturated ketones by the process of the present invention are olefins having 3 to about 20 carbon atoms, especially olefins having 3 to about 10 carbon atoms, including propylene, butylene, pentene, and higher straight-chain olefins, as well as cyclo-olefins, such as cyclohexene, cyclooctene, cyclododecene, and the like.

The reaction will normally be conducted at a temperature of about 150° C to about 400° C, and at pressures ranging from atmospheric to about 50 bars, with an olefin:steam molar ratio of about 1:30 to 1:0.3, preferably about 1.5:1 to 1:1. The thermostable carrier material may be silica or other conventional catalyst carriers, and normally the carrier will have a particle size of about 200 A to about 1000 A. The tin oxide and the molybdenum oxide will normally be in a molar ratio of about 1 : 1 of tin : molybdenum. Generally, tin oxide will be present in an amount of about 15 up to 300 weight percent, calculated as metal, based upon the weight of the carrier, and the amount of molybdenum oxide, calculated as metal, will be about 15 up to 170 percent by weight, based upon the weight of the carrier. The molybdenum oxide and the tin oxide will normally be present on the carrier in the form of particles having an average particle size of no greater than about 50 Angstroms, preferably about 25 to 40 Angstroms.

EXAMPLES OF THE INVENTION

In the following examples, sodium was used as the alkali metal and/or alkaline earth metal, but it will be readily appreciated that other metals falling within these categories may be substituted for the sodium with similar improvements in results.

EXAMPLE 1

60 liters of water, 6240 grams of urea, 10,500 grams of tin tetrachloride, and 1950 grams of finely divided microporous silica (available commercially under the tradename "Ketjen-SIL-201") were mixed in a 150 liter vessel and heated, with stirring, at the boiling point until a pH of 3.0 was reached. Then the mixture was cooled and washed repeatedly (with stirring, settling, and decanting, with a dilution factor of 1:3) with water which had a pH of 3 and to which 0.2% by weight of ammonium nitrate had been added, until the chlorine content of the suspension had decreased to less than 0.3 grams per liter. To the resulting suspension a neutral solution of 5200 grams of ammonium molybdate was added, and then the pH of the resulting suspension was adjusted to 3.0 by the addition of nitric acid.

The resulting suspension was divided into two equal parts, a part A and a part B. A solution of 90 grams of sodium nitrate in water (75 % concentration) was added to part B. The two separate parts were then dried and thereafter calcined for 1 hour at 650° C, using the same techniques. During the drying step, the promoted catalyst mass showed less caking tendency than the unpromoted mass.

The composition of the resulting catalyst was as follows:

| | Catalyst A | Catalyst B |
|---|---|---|
| $SnO_2$ | 46.5% by weight | 45.7% by weight |
| $MoO_3$ | 34.2% by weight | 34.7% by weight |
| $SiO_2$ | 19.3% by weight | 19.1% by weight |
| Na | absent | 0.45% by weight |

Propylene was converted into acetone in two separate experiments, one using catalyst A and the other using catalyst B. In each case, 20 grams of the supported catalyst were used. The reaction was conducted in a fluidized bed having a diameter of 2 cm and a bed height of 6 cm. The propylene:steam molar ratio was 0.5. 9.1 liters of propylene per hour were passed through the reactor, which was maintained at atmospheric pressure. The reactor temperature was maintained at 250° C. The catalyst was periodically regenerated by the process of copending application Ser. No. 88,467, acknowledged above.

Periodically, analysis of the reaction product was made by gas chromatography, and the selectivity and the efficiency of the process were derived from the resulting analytical figures. Selectivity for the desired product X was calculated as the member of olefin molecules converted into product X, divided by the total number of olefin molecules converted, times 100%. The process efficiency was calculated as the number of olefin molecules converted into the desired saturated ketone, divided by the total number of olefin molecules which disappeared during the conversion and during the catalyst regeneration, times 100%.

The results of this experiment are shown in Table I below.

EXAMPLE 2

Following the procedure of Example 1, a catalyst was prepared from 11.4 kg of tin chloride, 7.1 kg of urea, 6.7 kg of colloidal silica (obtainable commercially under the tradename "Ketjen SOL"), 100 liters of water and 5.1 kg of molybdenum trioxide in the form of ammonium molybdate. The catalyst suspension was divided into two equal parts, labelled part C and Part D, A solution of sodium nitrate and water, containing 76 grams of sodium, was added to Part D.

After the calcining operation, the composition of the resulting catalyst was as follows.

| | Catalyst C | Catalyst D |
|---|---|---|
| $SnO_2$ | 33.5% by weight | 34.4% by weight |
| $MoO_3$ | 27.3% by weight | 25.2% by weight |
| $SiO_2$ | 39.2% by weight | 39.8% by weight |
| Na | — | 0.65% by weight |

Using catalysts C and D, propylene was converted into acetone using the process described in Example 1. A gas mixture of 5.5. liters of propylene and 2.4 liters of water vapor per hour were passed through the reactor, and the reactor temperature was maintained at 250° C. The follow-results were obtained:

TABLE II

| | Catalyst C Selectivity (%) | | | | | Catalyst D Selectivity (%) | | | |
|---|---|---|---|---|---|---|---|---|---|
| Time (min.) | Oligomer | Isobutene | Acetone | Efficiency % | Time (min.) | Oligomer | Isobutene | Acetone | Efficiency % |
| 6 | 4.2 | 0.4 | 94.5 | | 6 | 0.8 | 0.0 | 95.4 | |
| 22 | 1.2 | 0.05 | 98.0 | 85.2 | 22 | 0.5 | 0.0 | 98.2 | 91.2 |
| 38 | 1.2 | 0.00 | 98.1 | | 38 | 0.4 | 0.0 | 98.7 | |

EXAMPLE 3

16 liters of water containing 300 grams of suspended, finely divided, microporous silicon dioxide, available commercially under the tradename "Ketjen Sil-201", were added to a 30 liter reactor equipped with baffle plates and having a diameter of 30cm. The reactor was provided with a stir having two 6-blade open turbine stirrers, of a diameter of 8 cm., mounted on an axial shaft at 10 and 20 cm, respectively, from the reactor bottom. The pH of the suspension in the reactor was adjusted to 3.0 by the addition of nitric acid. A solution of 1600 grams of tin tetrachloride and 10 liters of water was supplied at a constant rate of 1 liter per hour through a port in the vicinity of the lower turbine stirrer. An 8% ammonia aqueous solution was supplied through a second port in the vicinity of the upper turbine stirrer, with the rate of ammonia solution being supplied regulated by means of a valve controlled by a pH meter such that the pH of the suspension in the reactor was maintained at a value of 3.0 ± 0.1.

TABLE I

| CATALYST A | | | CATALYST B | | | |
|---|---|---|---|---|---|---|
| Time (min.) | Selectivity (%) oligomer | acetone | Efficiency (%) | Time (min.) | Selectivity (%) oligomer | acetone | Efficiency (%) |
| 5 | 5.74 | 89.3 | | 5 | 1.1 | 93.8 | |
| 13 | 3.14 | 95.4 | 83 | 14 | 1.7 | 95.9 | 87.7 |
| 29 | 1.57 | 96.9 | | 30 | 0.9 | 97.0 | |

After washing with water and decanting, using the procedure described in Example 1, until chlorine had been effectively removed, the suspension was centrifuged, producing 6024 grams of wet product. This centrifuged product was then suspended in a solution of 580 grams of molybdenum trioxide, in the form of an ammonium molybdate solution, in 10 liters of water. The resulting suspension was divided into two equal portions, labelled portion E and portion F.

Portion E was evaporated to dryness and then dried in a vacuum drying oven for 16 hours at 120° C and 10 mm Hg. Thereafter, the product was calcined in air for 1 hour at 650° C and atmospheric pressure. The resulting product was crushed and ground to produce a product from which a fraction having a particle size of 20–150 microns was removed by screening.

Portion F was processed in the same manner as portion E after a solution of sodium nitrate, containing 5 grams of sodium, in 100 ml of water had been added to it.

The composition of the resulting catalyst was as follows:

| | CATALYST E | CATALYST F |
|---|---|---|
| $SnO_2$ | 44.6% by weight | 44.4% by weight |
| $MoO_3$ | 29.1% by weight | 29.2% by weight |
| $SiO_2$ | 26.3% by weight | 26.1% by weight |
| Na | — | 0.3% by weight |

Using catalysts E and F, described above, transbutylene was converted into methylethyl ketone following the procedure of Example I. A gas mixture of steam:butene having a molar ratio of 5:2 was supplied to the reactor at the rate of 17.5 liters per hour. The reactor temperature was maintained at 250° C, and the processes produced the following results, as determined by the analytical method described for Example 1:

TABLE III

| | Catalyst E Selectivity (%) | | | | | Catalyst F Selectivity (%) | | | |
|---|---|---|---|---|---|---|---|---|---|
| Time (min.) | Oligomer | Acetone | Methyl Ethyl Ketone | Efficiency (%) | Time (min.) | Oligomer | Acetone | Methyl Ethyl Ketone | Efficiency (%) |
| 6 | 0.75 | 2.4 | 91.4 | | 6 | 0.4 | 0.5 | 94.7 | |
| 21 | 0.75 | 0.4 | 96.6 | 84.6 | 21 | 0.2 | 0.2 | 97.2 | 91.2 |
| 36 | 1.0 | 0.2 | 96.9 | | 36 | 0.2 | 0.1 | 97.6 | |

EXAMPLE 4

Example 1 was repeated, except the sodium nitrate was replaced by an equal amount, based on the weight of metal, of calcium acetate, with similar results.

The experimental results summarized above indicate that the use of the catalysts of the present invention results in a reduction of undesired by-products, allowing the process selectivity to be improved and the process efficiency to be increased. Obviously, it is also possible to use the catalyst of the present invention in a process involving the conversion of olefins into corresponding ketones in the presence of a gas containing molecular oxygen.

An especially advantageous process is that, in which the oxidation is effected by passing a mixture of the olefine, steam and at most 10 vol.% of oxygen, calculated on the volume of olefin, and optionally inert gas over a catalyst according to the invention, and periodically regenerating the catalyst by contacting it with an olefin-free oxygen-rich gas.

What is claimed is:

1. In a process for preparing ketones by contacting a mixture of at least one olefin and steam, wherein the olefin has from 3 to 20 carbon atoms, with a catalytic amount of a supported catalyst of tin oxide and molybdenum oxide, wherein the catalyst is supported on an inert, thermostable carrier material, and wherein the amount of said tin oxide, calculated as metal, in the catalyst is about 15 up to about 300 weight percent, based on the weight of carrier, and the amount of said molybdenum oxide, calculated as metal, in the catalyst is about 15 up to about 170 weight percent, based on the weight of the carrier material, the improvement comprising using said catalyst which further includes at least one metal oxide selected from the group consisting essentially of alkali metal oxides, alkaline earth metal oxides and mixtures thereof, in an amount, calculated as metal, of about 0.01 to about 5% by weight, based on the weight of the carrier material.

2. Process according to claim 19, wherein a mixture of said olefin and said steam, and at most 10 volume percent of oxygen is contacted with said catalyst, and the catalyst is alternatingly and periodically regenerated by contacting the catalyst with a substantially olefin-free oxygen-rich gas.

3. Process according to claim 2, wherein the mixture of olefin and steam is substantially free of oxygen.

4. Process according to claim 2, wherein said mixture of olefin and steam contains an inert gas.

5. Process according to claim 2, wherein said olefin-free oxygen-rich gas contains an inert gas.

6. Process according to claim 1, wherein the supported catalyst contains at least 30% by weight of a mixture of oxides of molybdenum and tin, wherein the molybdenum and tin are in the ratio, based on metal, of about 1:1.

7. Process according to clim 5, wherein said alkali metal is sodium.

8. The process according to claim 1, wherein the catalyst contains from 0.5 to 2% by weight of said metal compound, based on the weight of the carrier material.

9. The process according to claim 8, wherein said metal is sodium, potassium, and/or calcium.

10. The process according to claim 9, wherein said olefin is propylene, and said ketone is acetone.

11. The process according to claim 9, wherein said olefin is butylene, and said keton is methyl ethyl ketone.

* * * * *